(12) United States Patent
Takahashi

(10) Patent No.: US 8,248,464 B2
(45) Date of Patent: Aug. 21, 2012

(54) ENDOSCOPE SIGNAL PROCESSOR, ENDOSCOPE APPARATUS AND ENDOSCOPE SIGNAL PROCESSING METHOD

(75) Inventor: Kazumasa Takahashi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1650 days.

(21) Appl. No.: 11/638,755

(22) Filed: Dec. 14, 2006

(65) Prior Publication Data

US 2007/0139521 A1 Jun. 21, 2007

(30) Foreign Application Priority Data

Dec. 16, 2005 (JP) ................................. 2005-363695

(51) Int. Cl.
*H04N 7/18* (2006.01)
(52) U.S. Cl. ................ 348/65; 348/45; 348/68; 348/69; 348/70; 348/71; 348/72; 348/73; 348/74; 348/76; 348/222.1
(58) Field of Classification Search .................. 348/45, 348/65, 68–74, 76, 222.1
See application file for complete search history.

(56) References Cited

U.S. PATENT DOCUMENTS

| | | | | |
|---|---|---|---|---|
| 4,262,258 A | * | 4/1981 | Frosch et al. | 327/91 |
| 5,285,483 A | * | 2/1994 | Ogawa et al. | 375/376 |
| 6,567,114 B2 | * | 5/2003 | Takahashi et al. | 348/71 |
| 6,967,536 B2 | * | 11/2005 | Hayashida et al. | 331/1 A |
| 7,142,027 B2 | * | 11/2006 | Lee et al. | 327/158 |

FOREIGN PATENT DOCUMENTS

| | | |
|---|---|---|
| JP | 05-122058 | 5/1993 |
| JP | 06-086138 | 3/1994 |
| JP | 09-062222 | 3/1997 |
| JP | 2000-165759 | 6/2000 |

\* cited by examiner

*Primary Examiner* — Yasin Barqadle
*Assistant Examiner* — Van Kim T Nguyen
(74) *Attorney, Agent, or Firm* — Scully, Scott, Murphy & Presser, P.C.

(57) ABSTRACT

An endoscope signal processor to which an endoscope having an image pickup device is detachably connected has a phase-locked loop circuit in which a phase comparator compares a phase of a variable clock with that of a reference clock output from the image pickup device to generate a variable clock phase-synchronized with the reference clock. The processor includes a gate section opened or closed to input of the reference clock to the phase comparator, an operation control signal generation section which generates an operation control signal for setting the phase-locked loop circuit in a closed loop operable state during intermittent periods, and a sync timing setting section which synchronizes a timing of starting the generation of the operation control signal with a timing of input of the variable clock to the phase comparator at least within a predetermined time period shorter than the cycle of the variable clock.

17 Claims, 8 Drawing Sheets

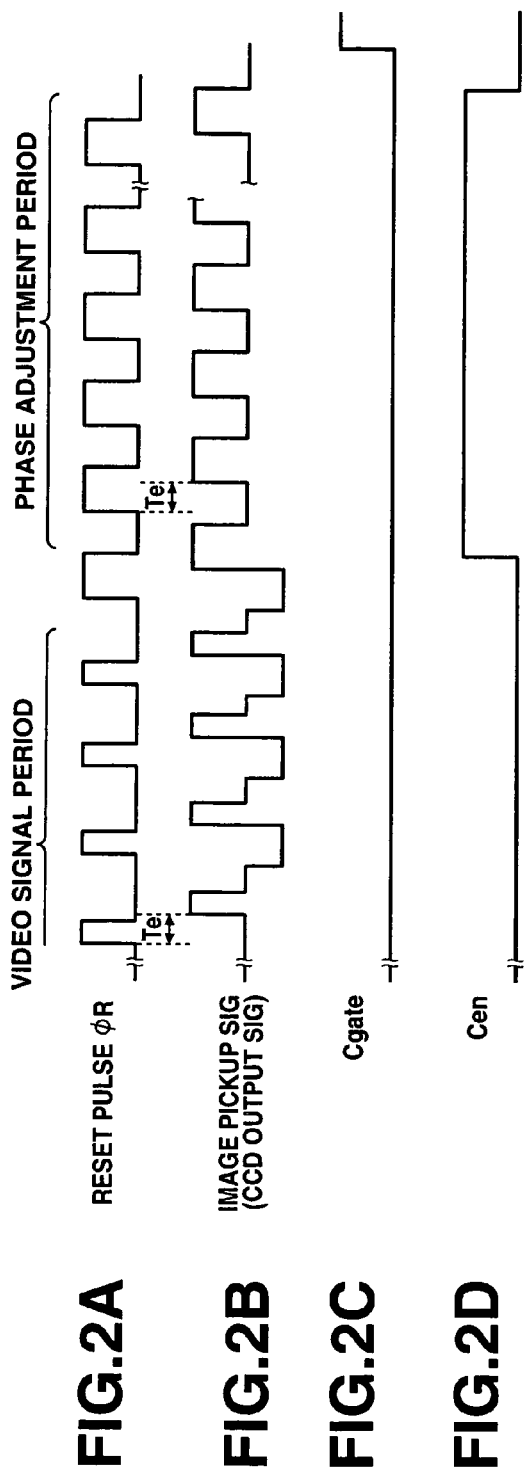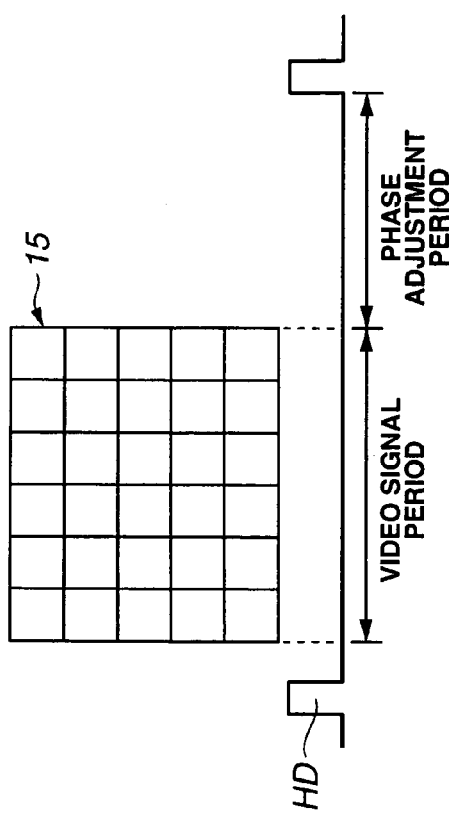

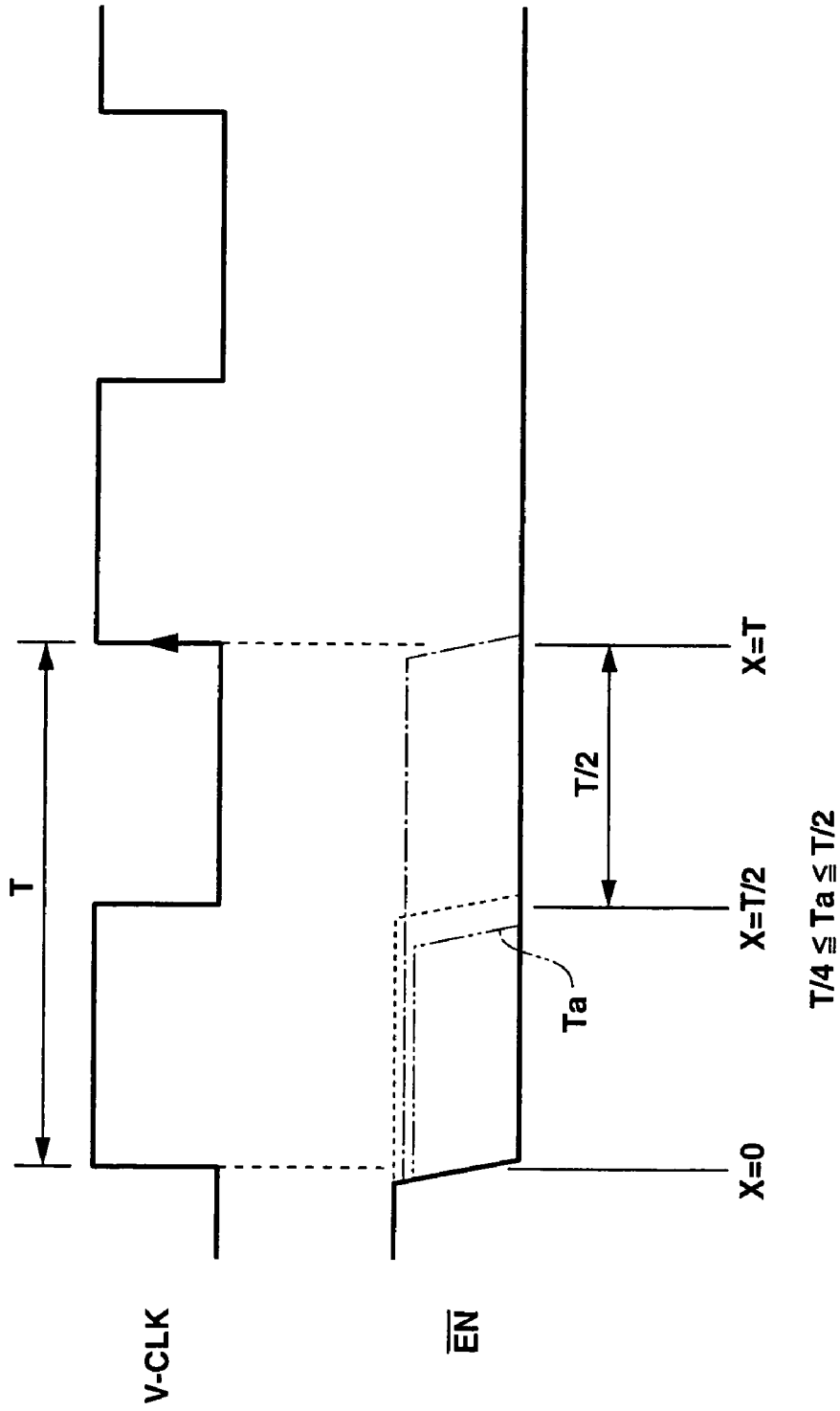

FIG.7A Cen 
FIG.7B V-CLK 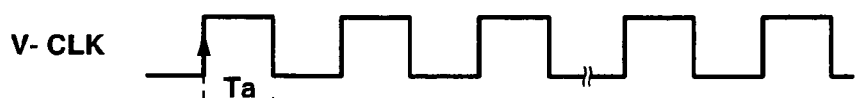
FIG.7C DL OUTPUT 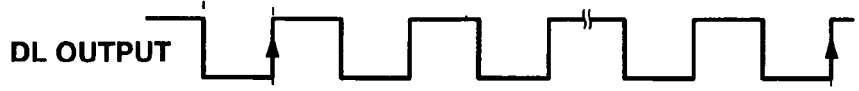
FIG.7D $\overline{EN}$ ($\overline{Q}$ OUTPUT) 
FIG.7E $\overline{EN}$ 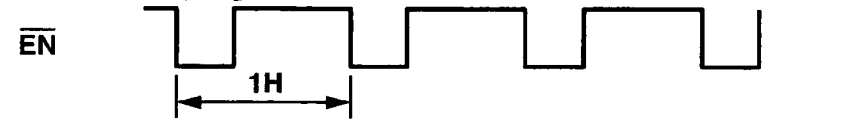
FIG.8
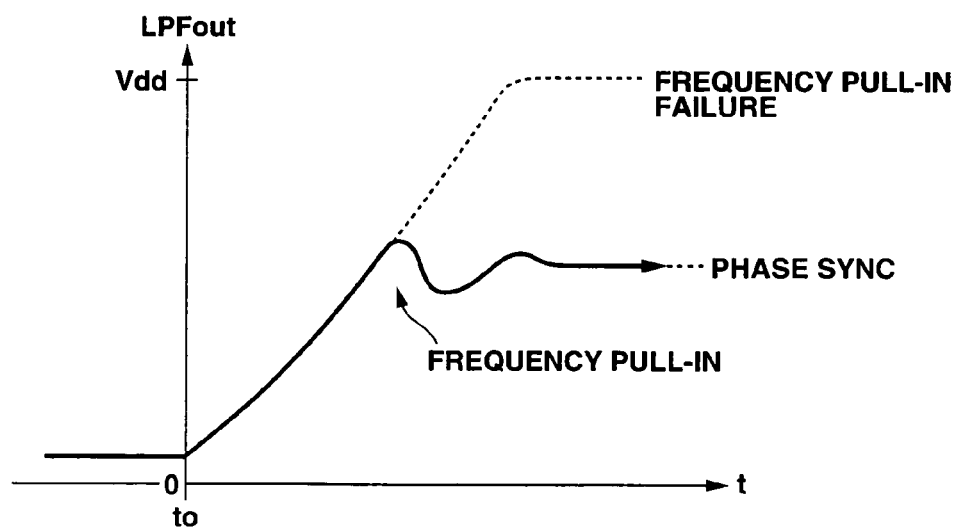
0>to R-CLK: off (GATE PORTION: CLOSED)
0≤to R-CLK: on (GATE PORTION: OPEN)

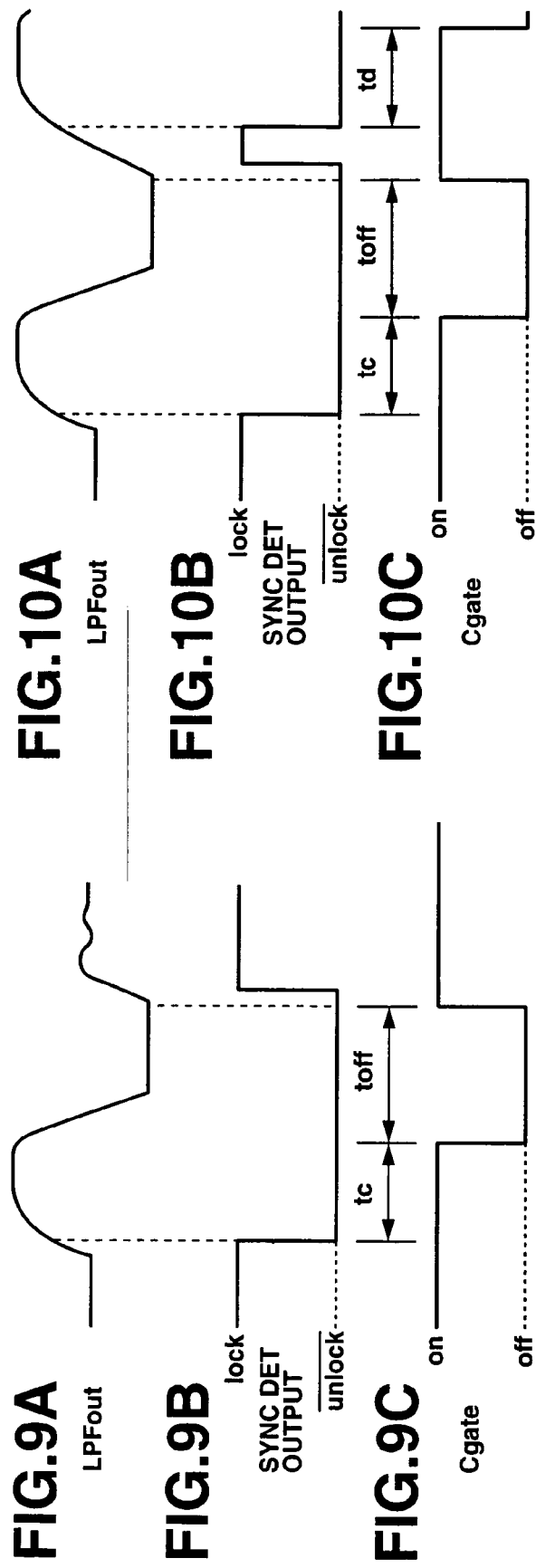

ENDOSCOPE SIGNAL PROCESSOR, ENDOSCOPE APPARATUS AND ENDOSCOPE SIGNAL PROCESSING METHOD

This application claims benefit of Japanese Application No. 2005-363695 filed on Dec. 16, 2005, the contents of which are incorporated by this reference.

BACKGROUND OF THE INVENTION

1. Field of the Invention

The present invention relates to an endoscope signal processor, endoscope apparatus and endoscope signal processing method in which signal processing adaptable even to an endoscope incorporating a high-pixel image pickup device is performed.

2. Description of the Related Art

In recent years, endoscopes incorporating image pickup devices have been put to wide use, for example, in the medical field. There are various kinds of endoscopes having insert portions of different lengths according to portions on which endoscopic inspections are to be performed or the like. For example, in such endoscopes, the length of a cable from an image pickup device to a signal processor for performing signal processing on the image pickup device to generate an endoscopic image varies.

If the cable length varies as described above, the amount of delay of transmission of a drive signal in the case of driving the image pickup device by the drive signal varies. The actual timing of input of an output signal output from the image pickup device to the signal processor also varies.

There is, therefore, a need to perform an adjustment operation for suitably setting, according to the amount of delay by the cable length, the timing of generation of sampling pulses for extracting actual signal components in the output signal from the image pickup device.

For example, Japanese Patent Laid-Open No. 6-86138 discloses a signal processor using a phase-locked loop circuit (PLL circuit) for enabling such an adjustment operation to be automatically performed.

In this disclosed related art, a signal is obtained by photoelectric conversion in an image pickup device having predetermined numbers of pixels arranged in horizontal and vertical directions, which photoelectric conversion is performed by applying a drive signal to the image pickup device. Readout of the signal from the image pickup device is performed as described below.

That is, this signal processor generates a gate signal in each of intermittent periods defined by setting as a phase adjustment period an empty-pixel period in which no pixels exist in each horizontal readout period, and sets the PLL circuit in an operable state to generate a timing signal phase-synchronized with reset pulses (as a reference clock) output from the image pickup device.

SUMMARY OF THE INVENTION

The present invention provides an endoscope signal processor including a phase-locked loop circuit in which a phase comparator compares a phase of a variable clock generated in a voltage controlled oscillation circuit with a phase of a reference clock output from an image pickup device incorporated in a detachably connected endoscope to generate a variable clock phase-synchronized with the reference clock, a gate section opened or closed to input of the reference clock to the phase comparator, an operation control signal generation section which generates an operation control signal for setting the phase-locked loop circuit in a closed loop operable state during intermittent periods, and a sync timing setting section which synchronizes a timing of starting the generation of the operation control signal with a timing of input of the variable clock to the phase comparator at least within a predetermined time period shorter than the cycle of the variable clock.

The present invention provides an endoscope apparatus including an endoscope having an image pickup device incorporated in a fore end portion of an elongated insert portion, and an endoscope signal processor having a connection portion to which the endoscope is detachably connected, a phase-locked loop circuit in which a phase comparator compares a phase of a variable clock generated in a voltage controlled oscillation circuit with a phase of a reference clock output from the image pickup device to generate a variable clock phase-synchronized with the reference clock, a gate section opened or closed to input of the reference clock to the phase comparator, an operation control signal generation section which generates an operation control signal for setting the phase-locked loop circuit in a closed loop operable state during intermittent periods, and a sync timing setting section which synchronizes a timing of starting the generation of the operation control signal with a timing of input of the variable clock to the phase comparator at least within a predetermined time period shorter than the cycle of the variable clock.

The present invention provides an endoscope signal processing method in order to generate a variable clock phase-synchronized with a reference clock output from an image pickup device incorporated in a detachably connected endoscope, by using a phase-locked loop circuit in which a phase comparator compares a phase of a variable clock generated in a voltage controlled oscillation circuit with a phase of the reference clock, includes a gate opening/closing control step of changing a gate at least from a closed state to an open state for input of the reference clock to the phase comparator, an operation control signal step of generating an operation control signal for setting the phase-locked loop circuit in a state of being capable of operating its closed loop during intermittent periods, and a sync timing setting step of synchronizing a timing of starting the generation of the operation control signal with a timing of input of the variable clock to the phase comparator at least within a predetermined time period shorter than the cycle of the variable clock.

BRIEF DESCRIPTION OF THE DRAWINGS

FIGS. 2A to 2D are timing charts showing reset pulses, an image pickup signal and other signals in a case where an endoscope is connected and driven;

FIG. 3 is a diagram for explaining a video signal period and a phase adjustment period;

FIG. 6 is a diagram for explaining synchronization of a variable clock (V-CLK) in a PLL circuit and an intermittent operation control signal ($\overline{EN}$) for setting a phase comparator in an operable state with predetermined timing which facilitates frequency pull-in;

FIGS. 7A to 7E are timing charts showing outputs from different sections during PLL operation;

FIG. 8 is a diagram showing a state of frequency pull-in when the PLL circuit is operated by changing a gate signal from an off state to an on state;

FIGS. 9A to 9C are diagrams for explaining the operation in a situation where the sync state is monitored and, if an out-of-synchronization state occurs, the gate signal is temporarily turned off and is thereafter turned on to perform frequency pull-in;

FIGS. 10A to 10C are diagrams for explaining the operation in the event of frequency pull-in failure;

DETAILED DESCRIPTION OF THE PREFERRED EMBODIMENTS

Embodiments of the present invention will be described with reference to the accompanying drawings.

First Embodiment

A first embodiment of the present invention will be described with reference to FIGS. 1 to 10C.

Figure 1:
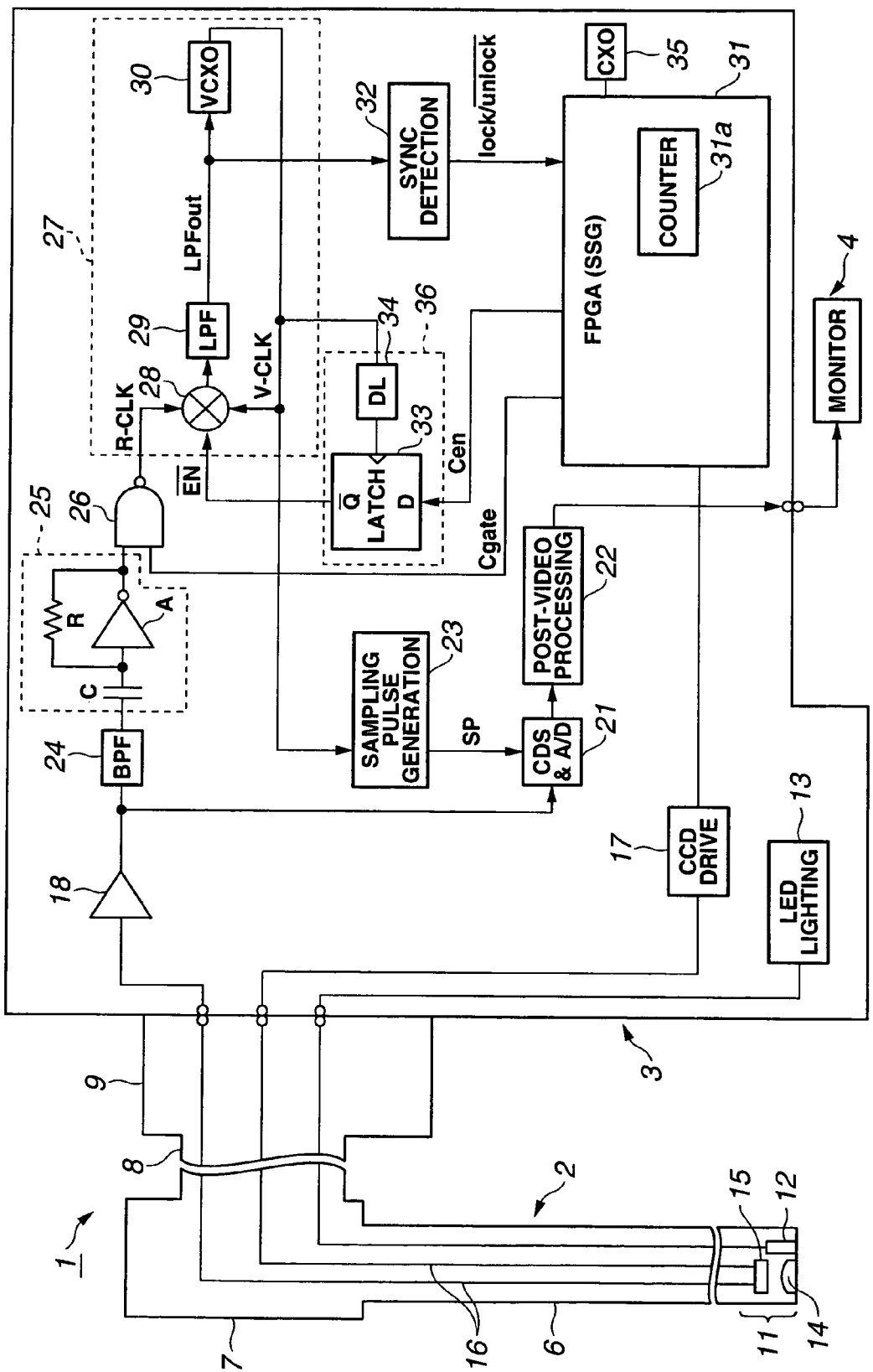
FIG. 1 is a block diagram showing the entire configuration of an endoscope system including a first embodiment of the present invention.

As shown in FIG. 1, an endoscope system 1 including the first embodiment of the present invention has an electronic endoscope 2 for performing an endoscopic inspection, a video processor 3 to which the electronic endoscope 2 is detachably connected, and which is provided as an endoscope signal processor for performing signal processing on an image pickup device mounted in the electronic endoscope 2, and a monitor 4 to which a video signal output from the video processor 3 is input to display as an endoscopic image an image captured with the image pickup device.

The electronic endoscope 2 has an elongated insert portion 6 to be inserted into a body cavity or the like, an operating portion 7 formed at the rear end (base end) of the insert portion 6, and a universal cable portion 8 extending from the operating portion 7. A connector 9 provided on the rear end of the universal cable portion 8 is detachably connected to the video processor 3.

In a fore end portion 11 provided in the insert portion 6 at the fore end of the same, an illumination window through which illumination light is emitted is provided. For example, a white light emitting diode (LED) 12 is mounted in the illumination window. An LED lighting circuit 13 provided in the video processor 3 supplies the white LED 12 with LED lighting power via a drive line to light the white LED 12. The white LED 12 thereby emits white illumination light.

An objective lens 14 is mounted in an observation window (image pickup window) provided adjacent to the illumination window. At a position at which an image is formed by the objective lens 14, a charge-coupled device (abbreviated as CCD) 15 for example is placed as an image pickup device.

The CCD 15 is connected to a CCD drive circuit 17 provided in the video processor 3 and to a front-end amplifier (abbreviated as FEA) 18 also provided in the video processor 3, via a signal cable 16 passed through the interior of the insert portion 6 and other portions.

A CCD drive signal output in certain cycles from the CCD drive circuit 17, including reset pulses φR, is applied to the CCD 15 via a drive line in the signal cable 16. By the applied CCD drive signal, the CCD 15 performs photoelectric conversion to output accumulated signal charges as an image pickup signal (or CCD output signal). This image pickup signal is input to the FEA 18 via a signal line in the signal cable 16.

The CCD 15 in the system shown in FIG. 1 is a high-pixel CCD having a number of pixels about thrice the usual number of pixels. Accordingly, in this embodiment, the frequency of horizontal transfer pulses and reset pulses φR in this embodiment is set to a high frequency of about 30 MHz in contrast with that in the case of the usual number of pixels (about 10 MHz). While one electronic endoscope 2 is shown in FIG. 1, the signal processing system is formed by using a phase-locked loop (PLL) circuit 27 so that the video processor 3 shown in FIG. 1 is used in common with electronic endoscopes having different cable lengths including the length of the insert portion 6.

As shown in FIG. 2A, reset pulses φR in the CCD drive signal for example are output in synchronization with a horizontal transfer signal or the like (not shown). A CCD output signal (image pickup signal) delayed, for example, by a time period Te from each reset pulse φR as shown in FIG. 2B is input to the FEA 18.

In this case, a video signal period shown in an upper left section of FIG. 2A is a period during which the image pickup signal for a horizontal row of pixels in the CCD 15 is read out from the CCD 15. The waveform of the image pickup signal changes according to luminance information on the corresponding pixels.

A phase adjustment period shown in an upper right section of FIG. 2A shows a non-signal period (empty signal period) after the completion of readout of the signal for the horizontal row of pixels in the CCD 15 (or before readout) during which no luminance information exists. Also during this period, reset pulses φR are applied to the CCD 15, as shown in FIG. 2A. As a result, the output signal from the CCD 15 is output as a reference clock for PLL circuit input, as shown in FIG. 2B.

As shown in FIG. 2A or the like, the duty ratio of reset pulses φR is changed in the phase adjustment period to facilitate separation from the video signal period. However, this is for facilitating separation between the two periods and is not indispensable for phase adjustment.

Referring to FIGS. 2A to 2D, the video signal period for readout of the signal for the next horizontal row of pixels follows the phase adjustment period shown in the right-hand section.

That is, as shown in FIG. 3, the CCD 15 has predetermined numbers of pixels respectively arranged in horizontal and vertical directions. In this case, the video signal period is a period during which a horizontal row of pixels is read out by applying reset pulses φR or the like in the CCD drive signal in synchronization with a horizontal sync signal (abbreviated as HD in FIG. 3), and the phase adjustment period is an idle readout period immediately after the video signal period. The video signal period and the phase adjustment period thus recur.

As shown in FIG. 1, CCD output signals amplified by the FEA 18 are input to a correlative double sampling (CDS) and analog-to-digital (A/D) circuit 21. Signal portions in the image pickup signal are extracted and converted into a baseband signal by correlative double sampling in a CDS circuit portion. The baseband signal is converted into a digital signal in an A/D circuit portion. This digital signal is input to a post-video processing circuit 22. The post-video processing circuit 22 generates a video signal from this digital signal and outputs the video signal to the monitor 4.

To the above-described CDS circuit portion, sampling pulses SP synchronized with a variable clock V-CLK output from the PLL circuit 27 described below are supplied from a sampling pulse generation circuit 23.

By using sampling pulses SP, the CDS circuit portion samples signal portions in image pickup signals. By using sampling pulses SP, a feed-through portion and luminance information portion in the image pickup signal shown in FIG. 2B are respectively sampled and a signal representing the difference therebetween is extracted, thereby forming the baseband signal.

The CCD output signal amplified by the FEA 18 is passed through a band-pass filter (BPF) 24 band-restricted so as to extract reset pulses φR in the phase adjustment period (as a reference clock), and undergoes waveform shaping performed by a limiter amplifier 25.

The limiter amplifier 25 is constituted by, for example, an inverting amplifier A. A capacitor C for passage of an alternating current signal and a resistor R are connected between input and output terminals of the inverting amplifier A.

The reset pulse φR signal waveform-shaped by the limiter amplifier 25 is input as a reference clock R-CLK to a phase comparator 28 constituting the PLL circuit 27 via a reference clock gate (hereinafter abbreviated as R-gate) 26. The R-gate 26 is constituted by a NAND circuit for example. The R-gate 26 forms a gate section (gate means) for opening/closing the path for input of the reference clock R-CLK to the PLL circuit 27.

When an intermittent operation control signal $\overline{EN}$ described below is applied at "L" to the phase comparator 28, the phase comparator 28 performs a phase comparison operation. When the intermittent operation control signal $\overline{EN}$ becomes "H", the phase comparator 28 stops the phase comparison operation.

The phase comparator 28 compares the phase of the reference clock R-CLK input thereto via the R-gate 26 and the variable clock V-CLK output from a voltage-controlled oscillator (abbreviated as VCXO) 30, and outputs a signal corresponding to the phase difference therebetween to a low-pass filter (LPF) 29.

The LPF 29 outputs to the VCXO 30 a signal formed of a low-frequency component of the output signal from the phase comparator 28. This signal is output as an output signal LPFout of the LPF 29. The VCXO 30 outputs the variable clock V-CLK whose oscillation frequency changes according to (for example, generally in proportion to) the voltage value of the output signal LPFout from the LPF 29 applied to its input end.

That is, the VCXO 30 outputs to the phase comparator 28 the variable clock V-CLK whose frequency or phase corresponds to the voltage value of the output signal LPFout from the LPF 29. The VCXO 30 also outputs the variable clock V-CLK to the sampling pulse generation circuit 23.

In this embodiment, the PLL circuit 27 is a circuit for generating sampling pulses SP according to suitable timing in an adjustment-free manner even in a case where the cable length is changed. Since the frequency of the reference clock R-CLK is substantially constant (determined by the number of pixels of the CCD 15), a crystal oscillating element having high frequency stability is used in the VCXO 30 to generate the variable clock V-CLK.

That is, in this embodiment, the PLL circuit 27 is used for the purpose of phase-synchronizing the variable clock V-CLK with the phase of the reference clock R-CLK (the frequency of the reference clock R-CLK and the frequency of the variable clock V-CLK can therefore be considered to be substantially equal to each other even if the width of variation in which frequency of the variable clock V-CLK is changed is considered).

In this embodiment, the phase comparator 28 detects a timing discrepancy between the rising edges of the variable clock V-CLK and the rising edges of the reference clock R-CLK, i.e., the output timing phase difference between the two clocks. The phase comparator 28 outputs a signal corresponding to the phase difference to the LPF 29.

For example, if the timing of the rising edges of the variable clock V-CLK is in advance of the timing of the rising edges of the reference clock R-CLK, the voltage value of the output signal LPFout from the LPF 29 decreases in correspondence with the phase difference and the oscillation frequency of the variable clock V-CLK is thereby reduced to delay the timing of the rising edges of the variable clock V-CLK (the phase of the variable clock V-CLK is delayed to reduce the phase difference).

If the reference clock R-CLK and the variable clock V-CLK is in the reverse relationship, the oscillation frequency of the variable clock V-CLK of the VCXO 30 is increased (the phase of the variable clock V-CLK is advanced to reduce the phase difference).

Also, if, for example, the voltage value of the output signal LPFout from the LPF 29 is higher, the frequency of the variable clock V-CLK is increased (that is, the phase is advanced).

The R-gate 26 performs opening/closing control on the operation to input the reference clock R-CLK to the phase comparator 28 according to an R-gate opening/closing control signal Cgate from a field programmable gate array (FPGA) 31 constituting the reference signal generation circuit (SSG). That is, in this embodiment, selection between the state in which the reference clock R-CLK is input to the phase comparator 28 of the PLL circuit 27 and the state in which reference clock R-CLK is not input to the phase comparator 28 of the PLL circuit 27 is enabled to ensure that a frequency pull-in operation can be smoothly or rapidly performed by the PLL circuit 27.

When the R-gate opening/closing control signal Cgate becomes "opening", the reference clock R-CLK is input to the phase comparator 28 and the phase comparator 28 makes phase comparison between the variable clock V-CLK and the reference clock R-CLK during a period during which the intermittent operation control signal $\overline{EN}$ becomes "L" intermittently.

The timing by which the variable clock V-CLK is input to the phase comparator 28 and by which the phase comparator 28 starts phase comparison with the reference clock R-CLK coincides with the timing by which the intermittent operation control signal $\overline{EN}$ becomes "L". This timing (also referred to as sync timing) is set so that the phase of the variable clock V-CLK (more specifically, the rising edge of the clock) is within a predetermined time period shorter than the cycle of the clock.

Thus, it is ensured that frequency pull-in can be performed with stability when the frequency pull-in operation is first started, and that even in a case where the frequency pull-in ends in failure or pull-in is cancelled, the frequency pull-in operation by the PLL circuit 27 can be again performed in a suitable state by closing the R-gate 26 and by thereafter opening the R-gate 26.

The R-gate opening/closing control signal Cgate is set to "opening" or "closing" (turned on/off), for example, in a period other than the phase adjustment period, as shown in FIG. 2C. For example, the R-gate opening/closing control signal Cgate is set to "opening" (that is, the reference clock R-CLK to the phase comparator 28 is shut off) during some phase adjustment periods, as shown in FIG. 2C. The PLL circuit 27 is thereby set in such a state that the output signal LPFout from the LPF 29 sticks to the ground side.

In this state, (because the reference clock R-CLK is not input to the phase comparator 28) the variable clock V-CLK is set (preset) in a most-delayed phase state corresponding to one end of a variable phase adjustment range (or a variable frequency range).

(As described below) when in this state the R-gate opening/closing control signal Cgate is set to "opening" (the reference clock R-CLK is input to the phase comparator 28), the frequency pull-in operation is substantially started (of course in the period during which the intermittent operation control signal $\overline{EN}$ is "L").

As described above, the (sync) timing setting ensures that the variable clock V-CLK can be smoothly phase-synchronized with the reference clock R-CLK in the process in which the variable clock V-CLK changes from the most delayed phase state at one end in the direction of advancement of the phase state in terms of frequency.

The output signal LPFout from the LPF 29 is input to a sync detection circuit (or pull-in detection circuit) 32. The sync detection circuit 32 performs detection from the level of the output signal LPFout as to whether the PLL circuit 27 is in the phase-synchronized state, in the frequency pull-in state (locked) state or in the non-pull-in state ($\overline{unlock}$), i.e., phase synchronization failure, and outputs the corresponding detection signal to the FPGA 31.

The FPGA 31 inputs the detection signal from the sync detection circuit 32 to a counter circuit 31a which is, for example, provided in the FPGA 31, counts the number of clock pulses from the oscillator 35 by using the counter circuit 31a, and monitors the time period during which the phase synchronized state is maintained.

If the non-phase-synchronized state continues beyond a predetermined time period tc (shown in FIG. 9C described below), based on the output from the counter circuit 31a the FPGA 31 performs the control operation including closing the R-gate 26 by setting the R-gate opening/closing control signal Cgate to "closing" (off), and thereafter opening the R-gate 26 by setting the R-gate opening/closing control signal Cgate to "opening" (on) to enable the reference clock R-CLK to be input to the phase comparator 28 of the PLL circuit 27.

Thus, it is made possible to again perform the frequency pull-in operation by the above-described PLL circuit 27. Also in an initial state after powering on, the FPGA 31 performs the control operation including turning off the R-gate opening/closing control signal Cgate and thereafter turning on this signal, and performs the frequency pull-in operation using the process by which frequency pull-in can be easily performed.

Figure 4:
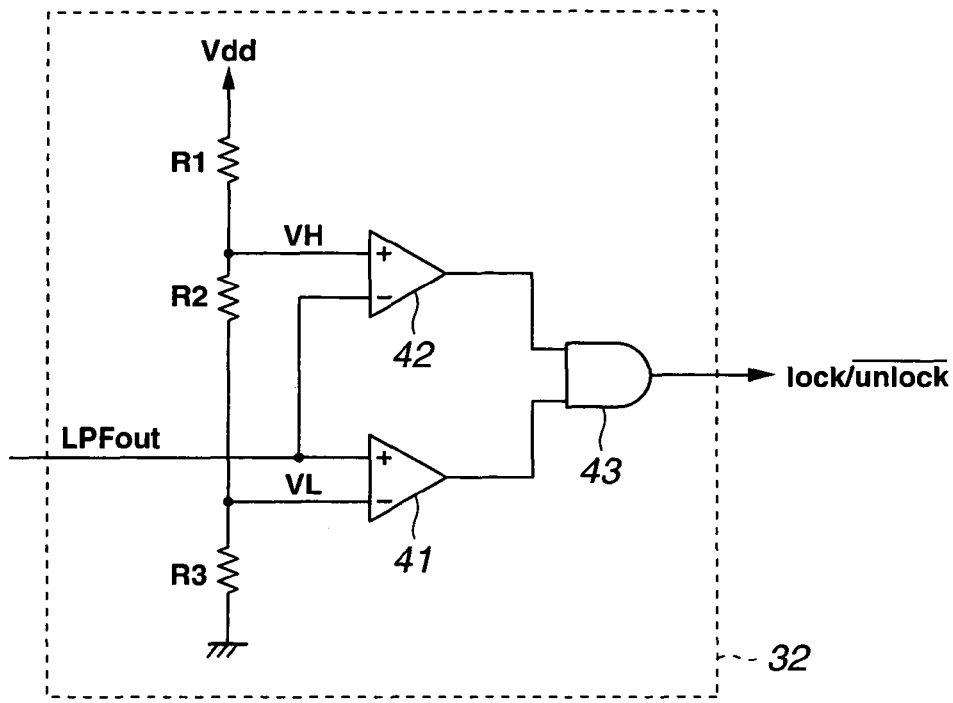
FIG. 4 is a circuit diagram showing an example of a configuration of a sync detection circuit.

FIG. 4 shows an example of a configuration of the sync detection circuit 32. The sync detection circuit 32 shown in FIG. 4 is constituted by a window comparator. To an inverting input terminal of a first comparator 41, a voltage VL obtained by dividing a power supply voltage Vdd between resistors R1 and R2 and a resistor R3 is applied. To a non-inverting input terminal of a second comparator 42, a voltage VH obtained by dividing the power supply voltage Vdd between the resistor R1 and the resistors R2 and R3 is applied.

The output signal LPF out from the LPF 29 is input to a non-inverting input terminal of the first comparator 41 and to an inverting input terminal of the second comparator 42. Output signals from the first and second comparators 41 and 42 are input to an AND circuit 43. The AND circuit 43 outputs a sync detection signal (or pull-in detection signal) lock/$\overline{unlock}$.

Figure 5:
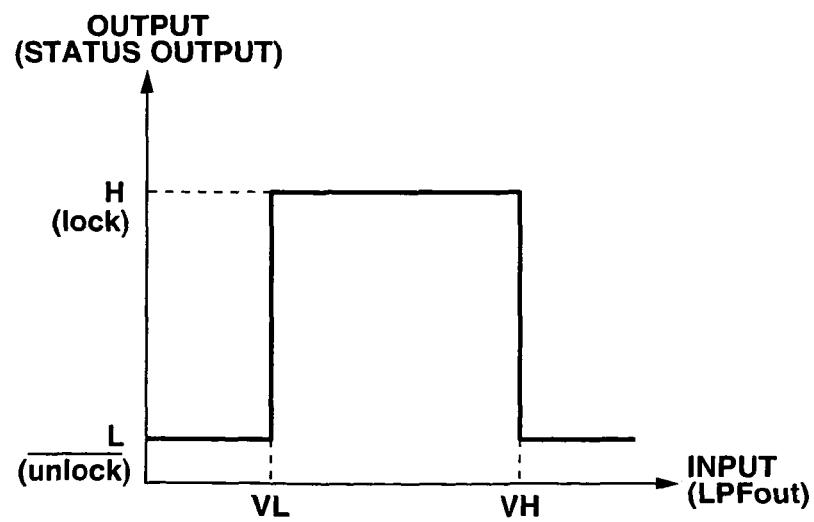
FIG. 5 is a diagram for explaining the operation of the circuit shown in FIG. 4.

That is, as shown in FIG. 5, the window comparator outputs $\overline{unlock}$ at "L" when the level of the output signal LPFout output from the LPF 29 and input to the window comparator is lower than the voltage VL. The window comparator also outputs $\overline{unlock}$ at "L" when the level of the output signal LPF out from the LPF 29 is higher than the voltage VH.

When the level of the output signal LPFout from the LPF 29 is between the voltages VL and VH, the window comparator outputs the sync detection signal lock at "H".

Thus, the sync detection circuit 32 outputs to the FPGA 31 the detection signal as to whether or not the PLL circuit 27 is in the pull-in state. The FPGA 31 monitors whether or not the PLL circuit 27 is in the synchronization state from the output signal from the sync detection circuit 32, and restarts the frequency pull-in operation again if the asynchronous state continues beyond the predetermined time period tc.

In this embodiment, a timing setting is made to ensure that when the frequency pull-in operation can be suitably performed when it is started by the PLL circuit 27 in the phase adjustment period.

Accordingly, the FPGA 31 outputs a control signal Cen to a latch circuit 33, whereby the intermittent operation control signal $\overline{EN}$ is applied to the phase comparator 28 as an operation control signal for starting the frequency pull-in operation by the PLL circuit 27. The control signal Cen is output so as to cover the intermittent phase adjustment period, as shown in FIG. 2D. The FPGA 31 and the latch circuit 33 form an operating control signal generation section for setting the PLL circuit 27 in the PLL operation state during the intermittent period.

The control signal Cen is applied to a D input terminal of the latch circuit 33. The variable clock V-CLK from the VCXO 30 is applied to a clock input terminal of the latch circuit 33 by timing delayed by a predetermined delay time Ta by a delay circuit (abbreviated as DL in FIG. 1) 34. The latch circuit 33 and the delay circuit 34 form a sync timing setting section 36.

In the phase adjustment period, the control signal Cen becomes "H" and the intermittent operation control signal $\overline{EN}$ is applied from a Q output terminal of the latch circuit 33 to the phase comparator 28 by the timing with the delay time Ta of the delay circuit 34 from the timing of the rising edge of the variable clock V-CLK first output from the VCXO 30 after the timing by which the control signal Cen becomes "H". The phase comparator 28 then starts the phase comparison operation.

That is, in a case where the PLL circuit 27 intermittently starts the frequency pull-in operation by the phase comparison operation of the phase comparator 28, the timing by which the intermittent operation control signal $\overline{EN}$ is applied to the phase comparator 28 is set by the delay circuit 34 and the latch circuit 33.

In this case, the timing is set so that the intermittent operation control signal $\overline{EN}$ is synchronized with the timing of the rising edge of the variable clock V-CLK in the predetermined time period. This timing setting will be described with reference to FIG. 6.

FIG. 6 shows details of the timing of the rising edge of the variable clock V-CLK and the timing of the falling edge of the intermittent operation control signal $\overline{EN}$ If the delay time set by the delay circuit 34 is X, the falling edges of the intermittent operation control signal $\overline{EN}$ with respect to X=0, X=T/2, and X=T are indicated by the solid line, the dotted line, and the dot-dash line, respectively, in FIG. 6.

The input to the delay circuit 34 for setting the delay time X is the variable clock V-CLK in the case shown in FIG. 6.

However, the reference clock R-CLK may be input in place of the variable clock V-CLK. (The value of the delay time X is changed in this case.)

Ordinarily, in the intermittent operation type of PLL circuit, the state defined by X=T/2 in FIG. 6 is the most desirable optimum condition if both frequency pull-in and low phase noise are to be attained.

In the case of deviation from the optimum condition, the output signal LPFout from the LPF 29 when frequency pull-in is started tends to stick to the power supply voltage Vdd side or the ground side, and degradation in frequency pull-in characteristics results.

In the state defined by X=T/2, i.e., under the above-described optimum condition, the output signal LPFout tends to be set to a medium value thereof and the facility with which follow-up to the input reference clock is quickly performed regardless of the phase of the reference clock.

In the case of deviation from the optimum condition, if, for example, X<T/2, the output signal LPFout tends to stick to the power supply voltage Vdd side. Conversely, if X>T/2, the output signal LPFout tends to stick to the ground side.

Consequently, quickly making a transition to the frequency pull-in state from the non-synchronized state requires setting a wide-band loop characteristic while sacrificing phase noise characteristics, or setting a low-band loop characteristic to ensure the phase noise characteristics. It is also necessary to set the delay time X to which the fall of the intermittent operation control signal $\overline{EN}$ is timed as described above to X=T/2 with substantially high accuracy in order to attain the desirable frequency pull-in state.

In this embodiment, a low-band loop characteristic is set in order to stabilize the operation after frequency pull-in, i.e., to ensure a low-phase-noise characteristic. Also, a sync timing setting is made on a practical level because it is difficult to ensure the above-described X=T/2 with high accuracy, due to problems in terms of device variation and temperature characteristics for example.

That is, in this embodiment, if the delay time X set by the delay circuit 34 is Ta, Ta is set to about $T/4 \leq Ta \leq T/2$ as shown in FIG. 6; a sync timing condition setting relaxed from the optimum condition is made.

This sync timing setting on a practical level and the above-described frequency pull-in process of closing from opening the R-gate 26 by the gate section ensure that frequency pull-in can be smoothly performed with a simple arrangement. A setting to about $0 \leq Ta \leq T/2$ may be made under a further relaxed sync timing setting condition.

Thus, in this embodiment, a sync timing setting is made such that the timing in the case of intermittently starting the frequency pull-in operation by the PLL circuit 27 (enabling the intermittent operation control signal $\overline{EN}$) and the variable clock V-CLK, i.e., a feedback signal to the phase comparator 28, are synchronized in a time period shorter than the cycle of the variable clock V-CLK.

In this arrangement, the constants of the LPF 29 are set so that the LPF 29 has a low-phase-noise low-band loop characteristic, thereby enabling a sync timing setting on a practical level to be made when frequency pull-in is performed and enabling frequency pull-in to be performed with stability by gate opening/closing by means of the gate section.

The FPGA 31 generates the above-described control signal by using a reference clock generated by the oscillator 35 using a crystal oscillating element having high oscillation frequency stability, and supplies the CCD drive circuit 17 with a timing signal as a reference at the time of generation of the CCD drive signal.

The operation of this embodiment will now be described. When an endoscopic inspection is performed, as shown in FIG. 1, the electronic endoscope 2 having an insert portion length suitable for the endoscopic inspection is used by being connected to the video processor 3.

The power supply (not shown) for the video processor 3 is turned on. The FPGA 31 of the video processor 3 then becomes operable and sends to the CCD drive circuit 17 the timing signal synchronized with the horizontal sync signal. The CCD drive circuit 17 outputs to the CCD 15 the CCD drive signal including reset pulses φR during the video signal period, as shown in FIG. 2A.

During the phase adjustment period, the CCD drive circuit 17 outputs, for example, only reset pulses φR to the CCD 15.

The CCD 15 outputs the image pickup signal shown in FIG. 2B. In this case, a delay shift of time period Te is generated between the reset pulses φR output from the CCD drive circuit 17 and the reset pulses φR input to the video processor 3 via the CCD 15 according to the insert portion length and the length of the universal cable portion 8, as shown in FIG. 2B.

The FPGA 31 changes the R-gate opening/closing control signal Cgate from the off state to the on state by timing, for example, after the beginning of the first phase adjustment period, as shown in FIG. 2C, thereby establishing a state in which the reference clock R-CLK can be input to the phase comparator 28 via the R-gate 26.

In the phase adjustment period, the FPGA 31 outputs the control signal Cen, as shown in FIG. 2D. With respect to the control signal Cen also shown in FIG. 7A, for example, in a case where the variable clock V-CLK is in a state such as shown in FIG. 7B, the output from the delay circuit 34 has a waveform delayed by the predetermined time Ta corresponding to the amount of delay by the delay circuit 34 from the variable clock V-CLK, as shown in FIG. 7C.

By the timing of the rising edge of the output signal rising first through the delay circuit 34 after the control signal Cen has become "H", the intermittent operation control signal $\overline{EN}$ shown in FIG. 7D is applied from the latch circuit 33 to the phase comparator 28.

By the application of the intermittent operation control signal $\overline{EN}$, the phase comparator 28 starts the phase comparison operation.

Since the control signal Cen shown in FIG. 7A becomes "H" during each (phase adjustment period shown in the upper section in FIG. 2A), the intermittent operation control signal shown in FIG. 7D also becomes "L" during each period Tcap corresponding generally to the phase adjustment period.

The PLL circuit 27 performs the frequency pull-in operation during the time period Tcap continuing after beginning from the time at which the intermittent operation control signal $\overline{EN}$ first becomes "L" in each horizontal period as shown in FIG. 7D. FIG. 7E shows, by changing the time scale, the time periods during which the intermittent operation control signal $\overline{EN}$ intermittently (periodically) becomes "L" in every horizontal period (1H), and during which the frequency pull-in operation is performed.

The intermittent operation control signal $\overline{EN}$ shown in FIG. 7D becomes "H" in correspondence with the timing by which the control signal Cen at "L" shown in FIG. 7A is latched at the rising edge of the variable clock V-CLK.

Because of the asynchronous state at the time of powering on, the sync detection circuit 32 outputs $\overline{unlock}$ and, accordingly, the R-gate opening/closing control signal Cgate becomes "L", so that the R-gate 26 is closed.

As shown in FIG. 2C, the R-gate opening/closing control signal Cgate changes from the off state to the on state, for example, after several or more recurrences of the intermittent operation control signal $\overline{\text{EN}}$ (the output signal LPFout from the LPF 29 sticking to the ground level in this state).

FIG. 8 shows the state of frequency pull-in by the PLL circuit 27 in a case where the time at which the R-gate opening/closing control signal Cgate changes from the off state to the on state is t0.

In an initial state when the intermittent operation control signal $\overline{\text{EN}}$ first becomes "L", the R-gate opening/closing control signal Cgate is still in the off state and, therefore, the reference clock R-CLK is not input to the phase comparator 28.

Accordingly, the output signal LPFout from the LPF 29 is sticking to the ground side based on the reception of the result of phase detection by the phase comparator 28. When the reference clock R-CLK is input at time t0, the output signal LPFout from the LPF 29 rises toward the power supply voltage Vdd from the ground level, as shown in FIG. 8.

In this case, a setting is made such that the fall timing of the intermittent operation control signal $\overline{\text{EN}}$ is synchronized with the variable clock V-CLK at about $T/4 \leqq Ta \leqq T/2$, as described above with reference to FIG. 6.

The following is an explanation of the reason why the output signal LPFout from the LPF 29 rises toward the power supply voltage Vdd and the reason why the phase synchronization is finally established.

With respect to the variable clock V-CLK input to the phase comparator 28, the frequency of occurrence of input to the phase comparator 28 of one of the reference clock R-CLK and the variable clock V-CLK prior to the other in the asynchronous state will be considered. Since $T/4 \leqq Ta \leqq T/2$, the frequency of occurrence of input of the reference clock R-CLK prior to the variable clock V-CLK (in phase advance) is higher. Under this bias effect, the PLL loop operates to change the output signal LPFout toward the power supply voltage Vdd and to thereby advance the phase of the variable clock V-CLK.

That is, the output signal LPFout is changed by the bias effect based on Ta until a point in the vicinity of the frequency pull-in region is reached, and a transition to the PLL circuit capture process generally referred to is thereafter made to establish phase synchronization.

Frequency pull-in is thus performed to hold the level of the output signal LPFout from the LPF 29 in the phase-synchronized state.

After establishment of the above-described phase-synchronized state, disengagement from the phase-synchronized state may occur due to some cause. Even in such an event, an operation to again set in the phase-synchronized state is performed as shown in FIGS. 9A to 9C.

When an out-of-phase-synchronization state occurs due to some cause after the phase-synchronized state as shown in FIG. 9B, the output signal LPFout from the LPF 29 is changed, for example, toward the power supply voltage level, as shown in FIG. 9A.

The out-of-phase-synchronization state is being monitored by the sync detection circuit 32. If the out-of-phase-synchronization state continues, for example, over a predetermined time period tc (about 200 mS for example) as shown in FIG. 9B, (FPGA 31) changes the R-gate opening/closing control signal Cgate from the on state to the off state, as shown in FIG. 9C. The reference clock R-CLK is not input to the phase comparator 28 thereafter. The level of the output signal LPFout from the LPF 29 then changes toward the ground level, as shown in FIG. 9A.

When the lapse of time during which the R-gate opening/closing control signal Cgate is off becomes longer than toff (e.g., about 200 mS) for example, the FPGA 31 changes the R-gate opening/closing control signal Cgate from the off state to the on state (see FIG. 9C). The output signal LPFout from the LPF 29 then rises from the ground level toward the power supply voltage Vdd, as described above with reference to FIG. 8. During this process, the frequency pull-in operation is smoothly performed.

When the R-gate opening/closing control signal Cgate is changed from the off state to the on state in the above-described operation, there is a possibility of failure to perform frequency pull-in. Therefore, the FPGA 31 monitors this operation through the output from the sync detection circuit 32. FIGS. 10A to 10C show an example of the operation in a case where frequency pull-in failure occurs when the operation shown in FIGS. 9A to 9C is performed.

The FPGA 31 monitors the state of the output signal from the sync detection circuit 32, as described above. If, as shown in FIG. 10C, the out-of-synchronization state ($\overline{\text{unlock}}$ state) continues, for example, for a predetermined time period td (e.g., about 200 mS) after the R-gate opening/closing control signal Cgate has been changed from the off state to the on state, the FPGA 31 returns the R-gate opening/closing control signal Cgate from the on state to the off state.

The FPGA 31 changes the R-gate opening/closing control signal Cgate from the off state to the on state after a lapse of time period toff to repeat frequency pull-in as described above with reference to FIGS. 9A to 9C.

When frequency pull-in is performed, the sampling pulse generation circuit 23 supplied with the variable clock V-CLK phase-synchronized with the reference clock R-CLK outputs to the CDS and A/D circuit 21 sampling pulses SP for sampling the image pickup signal in the video signal period, thereby enabling the CDS and A/D circuit 21 to extract signal portions in the image pickup signal with stability by the signal portion extraction timing.

Timing for extracting signal portions is thus performed with stability to obtain an endoscopic image of good image quality.

According to this embodiment, as described above, frequency pull-in can be smoothly performed with a simple arrangement in a state where a low-band loop characteristic for a low phase noise characteristic is set. The low-band loop characteristic can be set substantially independently of the capture range. Therefore, the present invention is highly advantageous in a case where the phase comparison frequency is high and the iteration cycle of intermittent operation is long.

The present invention can be implemented in a simple arrangement. Also, closed loop response can be set in a low-band loop characteristic for a low phase noise characteristic. Therefore, stable operation can be ensured after frequency pull-in and endoscopic images of good image quality can be successively obtained.

Second Embodiment

Figure 11:
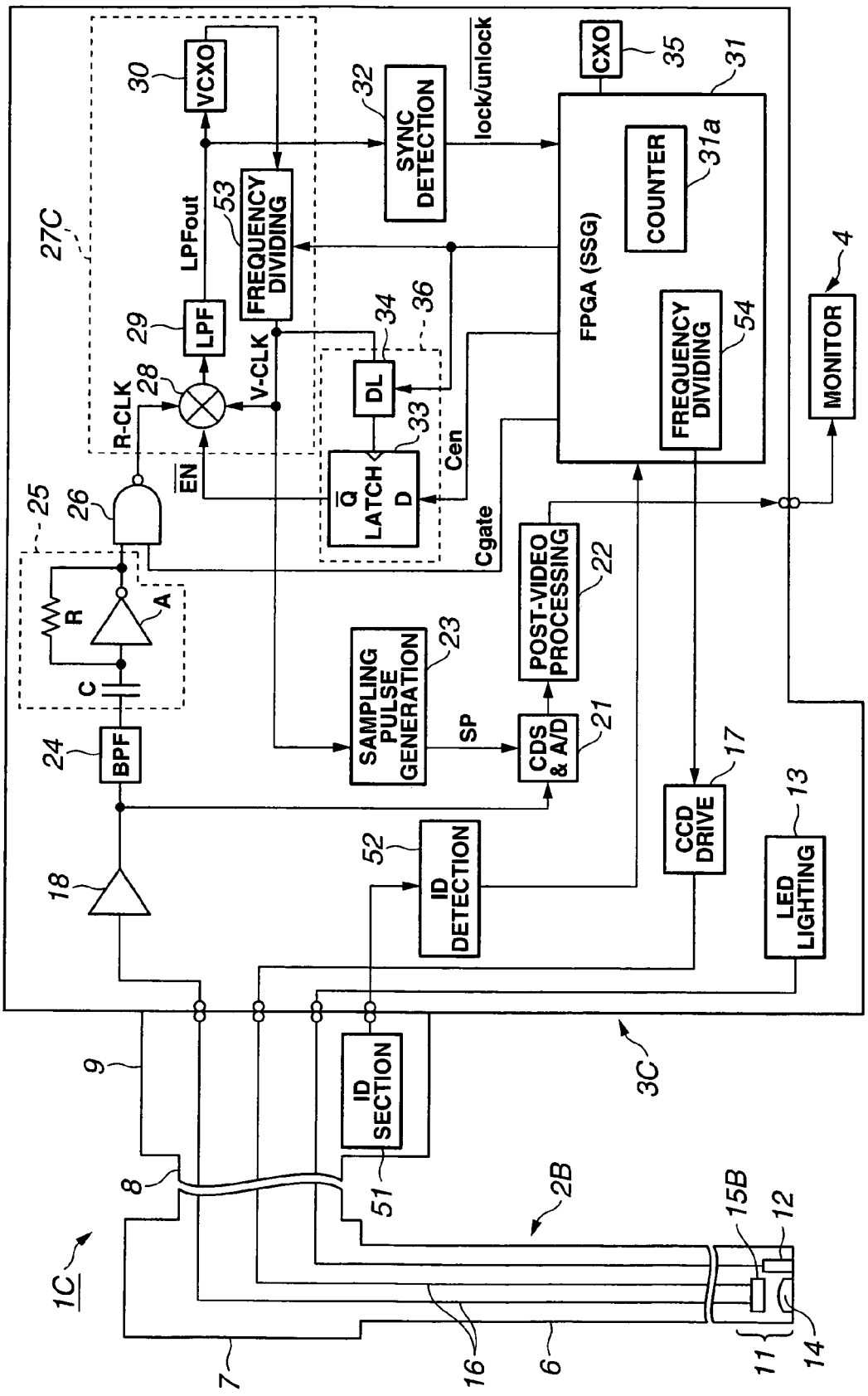
FIG. 11 is a block diagram showing the entire configuration of an endoscope system including a second embodiment of the present invention.

A second embodiment of the present invention will be described with reference to FIG. 11. FIG. 11 shows an endoscope system 1C including the second embodiment of the present invention. This endoscope system 1C includes a CCD 15B having a number of pixels different from that of the CCD 15 mounted in the electronic endoscope 2 in the endoscope system 1 shown in FIG. 1, such as to be adaptable to an electronic endoscope 2B. While the electronic endoscope 2B incorporating the CCD 15B is shown in FIG. 11, a video processor 3C also adaptable to the electronic endoscope 2 shown in FIG. 1 is used.

Therefore, each of the electronic endoscopes 2 and 2B has an ID section 51 which generates ID information for identifying the corresponding electronic endoscope and for identifying the number of pixels of the CCD mounted in the electronic endoscope. The ID section 51 is incorporated, for example, in the connector 9.

The video processor 3C in this embodiment incorporates an ID detection circuit 52 for detecting the ID information in each ID section 51. The detected ID information is input to the FPGA 31.

The video processor 3C shown in FIG. 11 uses a PLL circuit 27C obtained by providing a frequency dividing circuit 53 in the PLL circuit 27 in the video processor 3 shown in FIG. 1. The frequency dividing ratio of the frequency dividing circuit 53 is variably set by the FPGA 31 according to the number of pixels in the ID information.

The FPGA 31 also incorporates a frequency dividing circuit 54 which outputs to the CCD drive circuit 17 a timing signal frequency-divided by a frequency dividing ratio according to ID information including the number of pixels of the CCD 15 or 15B. That is, a common frequency dividing ratio is selected for the frequency dividing circuits 53 and 54 according to the number of pixels of the CCD actually driven.

The FPGA 31 changes the delay time Ta of the delay circuit 34 when the reference clock R-CLK and the variable clock V-CLK are changed according to the number of pixels of the CCD. More specifically, for example, a delay time Ta inversely proportional to the frequency dividing ratio is selected and set. If the change in the number of pixels is not so large, the same delay time Ta may be used in common without being changed.

The sampling pulse generation circuit 23 may change, according to the number of pixels of the CCD, if necessary, the amount of delay caused by an internal delay circuit or the like.

In other respects, the configuration is the same as that of the first embodiment. Components identical to those in the first embodiment are indicated by the same reference numerals, and the description for them will not be repeated.

According to this embodiment, even in a case where a CCD having a different number of pixels is used, a CCD drive signal is generated which is frequency-divided by the frequency dividing circuit 54 to enable the CCD having the different number of pixels to be suitably driven, and the frequency dividing circuit 53 in the PLL circuit 27C on the signal processing side for processing on the image pickup signal correspondingly divides the variable clock V-CLK and to enable phase comparison in the phase comparator 28.

Therefore, the system in this embodiment can be suitably adapted to an electronic endoscope incorporating the CCD having a different number of pixels in an adjustment free manner, as is that in the first embodiment. This embodiment also ensures the same advantages as those in the first embodiment in other respects.

In the above-described first and second embodiments, a device for opening/closing the input path for reference clock R-CLK to (the phase comparator 28 in) the PLL circuit 27 or 27C is formed by using the R-gate 26 provided between the limiter amplifier 25 and the phase comparator 28. However, an arrangement such as that in an example of a modification shown in FIG. 12 may alternatively be adopted.

Figure 12:
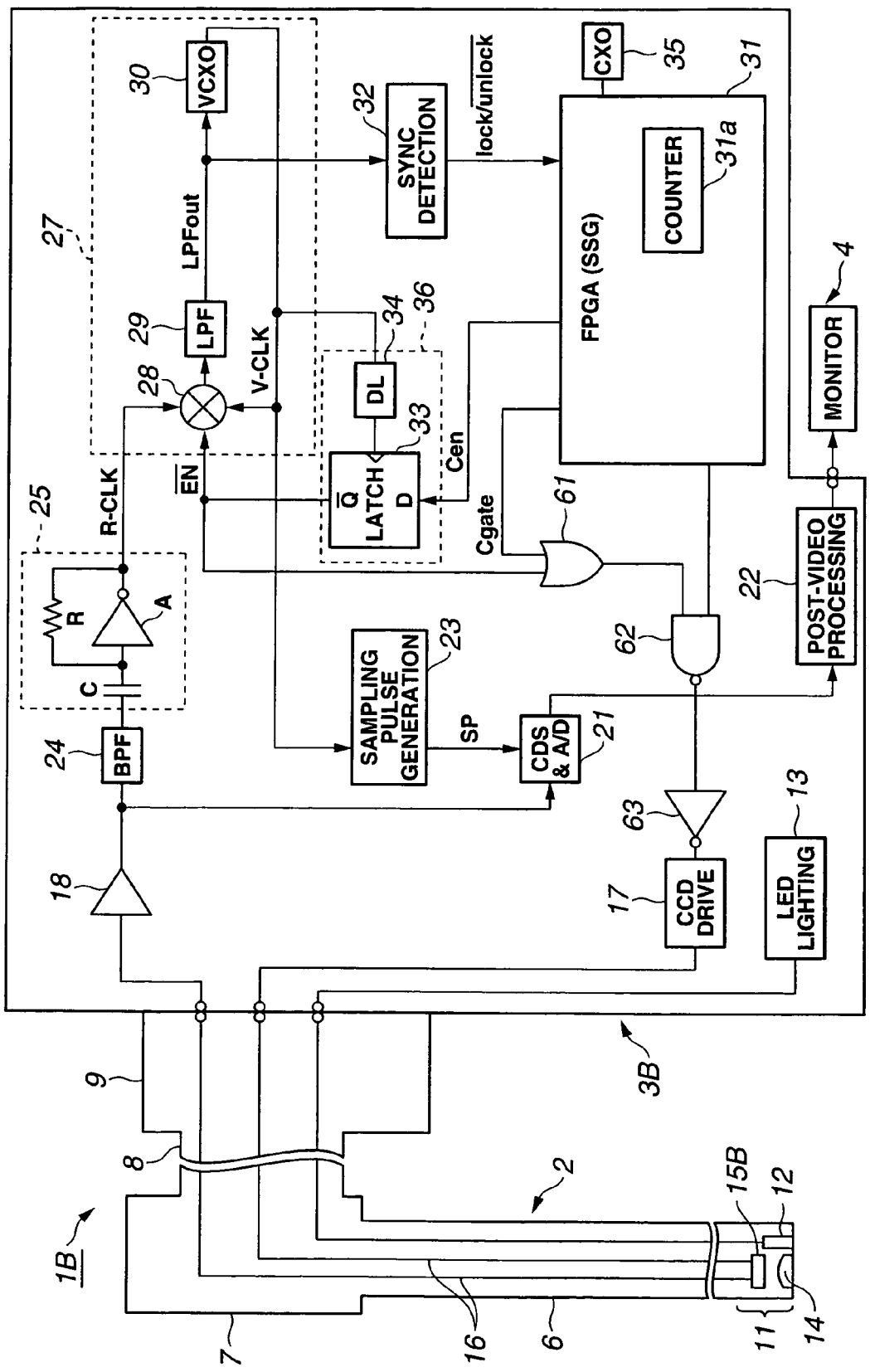
FIG. 12 is a block diagram showing the entire configuration of an endoscope system including an example of modification.

FIG. 12 shows the configuration of an endoscope system 1B in an example of a modification of the first embodiment. The video processor 3B in the endoscope system 1B has a gate circuit corresponding to the R-gate 26. This gate circuit is disposed between the FPGA 31 and the CCD drive circuit 17 in the video processor 3 shown in FIG. 1.

More specifically, the R-gate opening/closing control signal Cgate and the intermittent operation control signal $\overline{EN}$ are input to an OR circuit 61, and an output signal from the OR circuit 61 is input to a NAND circuit 62. The timing signal for generating the CCD drive signal as in the case of the first embodiment is also input to the NAND circuit 62. An output from the NAND circuit 62 is input to the CCD drive circuit 17 via an inverter circuit 63. An AND circuit may be used in place of the NAND circuit 62 to remove the inverter circuit 63.

In other respects, the configuration is the same as that of the first embodiment. Referring to FIG. 12, the gate formed by the NAND circuit 62 is open during a period when the intermittent operation control signal $\overline{EN}$ is "H", i.e., a video signal period defined by removing a time period in the vicinity of the phase adjustment period. The CCD 15 is driven in this video signal period in the same manner as in the first embodiment.

In the phase adjustment period during which the intermittent operation control signal $\overline{EN}$ is "L", determination is made as to whether or not the timing signal (reset pulses in this case) are output from the FPGA 31 to the CCD drive circuit 17 according to whether or not the FPGA 31 outputs the R-gate opening/closing control signal Cgate. Gate opening/closing control as to whether or not the reset pulses are input as the reference clock R-CLK to the phase comparator 28 via the CCD 15 is performed thereby.

In this example of a modification, the gate section performs an operation to open/close the input path for the reference clock R-CLK to the CCD drive circuit 17 in each phase adjustment period. The operation including frequency pull-in is substantially the same as that in the first embodiment. Also, substantially the same effects as those in the first embodiment are obtained. Thus, according to the present invention, frequency pull-in can be performed with a simple arrangement in a state where a low-phase noise characteristic is set.

When the phase sync operation is started in the embodiments described above, for example, in the first embodiment, the FPGA 31 closes the gate section and controls the phase state of the variable clock V-CLK so that the variable clock V-CLK is preset in the most delayed phase state in the phase adjustment range.

When the gate section is opened, the timing of enabling phase comparison of the intermittent operation control signal $\overline{EN}$ by the phase comparator 28 is set by being synchronized with T/2 or less (more preferably T/4 to T/2) of the cycle T of the clock rising edge of the variable clock V-CLK. This timing setting has the effect of changing the variable clock V-CLK in the direction of phase advance in terms of frequency.

The present invention is not limited to this. For example, the phase state of the variable clock V-CLK may be smoothly phase-synchronized in the process of opening the gate section and changing the variable clock V-CLK in the direction of phase delay in terms of frequency from the state of being preset in the most phase-advanced condition.

In such a case, the timing of enabling phase comparison of the intermittent operation control signal $\overline{EN}$ by the phase comparator 28 is set by being synchronized with T/2 or more (more preferably T/2 to 3T/4) of the cycle T of the clock rising edge of the variable clock V-CLK.

To preset the phase state of the variable clock V-CLK in the most phase-advanced state in such a case, an offset voltage may be applied, for example, to the VCXO 30 according to the timing by which the gate section is closed. (Needless to say, the application of this offset voltage is stopped when the gate section is opened.)

Other possible embodiments of the present invention constructed, for example, by combing portions of the above-described embodiments and other components can belong to the present invention.

What is claimed is:

1. An endoscope signal processor comprising:
a phase-locked loop circuit in which a phase comparator compares a phase of a variable clock generated in a voltage controlled oscillation circuit with a phase of a reference clock output from an image pickup device incorporated in a detachably connected endoscope to generate a variable clock phase-synchronized with the reference clock;
a gate section configured to open or close an input path from the reference clock to the phase comparator;
an operation control signal generation section which generates an operation control signal for setting the phase-locked loop circuit in a closed loop operable state during intermittent periods;
a sync timing setting section which synchronizes a timing of starting the generation of the operation control signal with a timing of input of the variable clock to the phase comparator at least within a predetermined time period shorter than half of the cycle T of the variable clock; and
a sync detection section which performs detection as to whether or not the variable clock is phase-synchronized with the reference clock,
wherein, the sync timing setting section sets the predetermined time period so that the timing of starting the generation of the operation control signal is set within a range from T/4 to less than T/2 from the timing of input of the variable clock to the phase comparator so as to operate, when set to an operation state of the closed loop, in a direction to decrease, in terms of frequency, a relative phase difference of the variable clock with respect to the reference clock before the operation state of the closed loop.

2. The endoscope signal processor according to claim 1, wherein the sync detection section monitors whether or not the time period during which the variable clock is not phase-synchronized with the reference clock exceeds a predetermined time period, and temporarily closes the gate section if the time period during which the variable clock is not phase-synchronized with the reference clock exceeds the predetermined time period.

3. The endoscope signal processor according to claim 1, wherein the sync detection section monitors whether or not the time period during which the variable clock is not phase-synchronized with the reference clock exceeds a predetermined time period, and temporarily closes and thereafter opens the gate section if the time period during which the variable clock is not phase-synchronized with the reference clock exceeds the predetermined time period.

4. The endoscope signal processor according to claim 1, wherein the frequency dividing ratio of a frequency dividing circuit constituting the phase-locked loop circuit is controlled according to information on a kind of the image pickup device incorporated in the endoscope.

5. The endoscope signal processor according to claim 1, wherein the operation control signal generation section generates the operation control signal from an output signal from the image pickup device in each horizontal period by setting as each of the intermittent periods a time period not used for readout of pixels in the image pickup device.

6. The endoscope signal processor according to claim 1, further comprising a correlative double sampling processing circuit which performs correlative double sampling on an output signal from the image pickup device by sampling pulses synchronized with the variable clock.

7. The endoscope signal processor according to claim 1, further comprising a reference clock generation section which generates, as the reference clock, from an output signal from the image pickup device, reset pulses in an image pickup device drive signal applied to the image pickup device in a time period not used for readout of pixels in the image pickup device, wherein the generated reference clock is input to the gate section.

8. The endoscope signal processor according to claim 1, wherein, before an operation to phase-synchronize the variable clock with the reference clock is performed, the gate section is closed and the variable clock is preset in a phase state at one end of a range of phase adjustment of the variable block.

9. The endoscope signal processor according to claim 8, wherein the gate section is opened from the closed state to start the operation to phase-synchronize the variable clock with the reference clock, whereby the phase state of the variable clock is changed to a phase state at the other end in terms of frequency.

10. The endoscope signal processor according to claim 1, wherein the gate section opens and closes input of the reference clock to the phase comparator by controlling opening/closing of a timing signal for generating a reference clock, the timing signal being inputted to an image pickup device drive circuit for generating an image pickup device drive signal that causes the reference clock to be outputted from the image pickup device.

11. The endoscope signal processor according to claim 1, wherein the sync timing setting section sets the predetermined time period so that the timing of starting the generation of the operation control signal is set within a range from T/4 to less than T/2 or a range greater than T/2 to not greater than 3T/4 from the timing of input of the variable clock to the phase comparator so as to operate, when set to an operation state of the closed loop, in a direction to decrease, in terms of frequency, a relative phase difference of the variable clock with respect to the reference clock before the operation state of the closed loop.

12. An endoscope apparatus comprising:
an endoscope having an image pickup device incorporated in a fore end portion of an elongated insert portion; and
an endoscope signal processor having:
a connection portion to which the endoscope is detachably connected,
a phase-locked loop circuit in which a phase comparator compares a phase of a variable clock generated in a voltage controlled oscillation circuit with a phase of a reference clock output from the image pickup device to generate a variable clock phase-synchronized with the reference clock,
a gate section configured to open or close an input path from the reference clock to the phase comparator, an operation control signal generation section which generates an operation control signal for setting the phase-locked loop circuit in a closed loop operable state during intermittent periods,
a sync timing setting section which synchronizes a timing of starting the generation of the operation control signal with a timing of input of the variable clock to the phase comparator at least within a predetermined time period shorter than half of the cycle T of the variable clock, and a sync detection section which performs detection as to whether or not the variable clock is phase-synchronized with the reference clock;

wherein, if the cycle of the variable clock is T, the sync timing setting section sets the predetermined time period so that the timing of starting the generation of the operation control signal is set within a range from T/4 to less than T/2 from the timing of input of the variable clock to the phase comparator so as to, when set to an operation state of the closed loop, operate in a direction to decrease, in terms of frequency, a relative phase difference of the variable clock with respect to the reference clock before the operation state of the closed loop.

13. The endoscope apparatus according to claim 12, wherein the sync detection section monitors whether or not the time period during which the variable clock is not phase-synchronized with the reference clock exceeds a predetermined time period, and temporarily closes and thereafter opens the gate section if the time period during which the variable clock is not phase-synchronized with the reference clock exceeds the predetermined time period.

14. The endoscope apparatus according to claim 12, wherein the frequency dividing ratio of a frequency dividing circuit constituting the phase-locked loop circuit is further controlled according to information on the kind of the image pickup device incorporated in the endoscope.

15. The endoscope apparatus according to claim 12, wherein a plurality of endoscopes differing in the length of the insert portion or in the number of pixels of the image pickup device from each other are selectively connected to the endoscope signal processor.

16. An endoscope signal processing method, in order to generate a variable clock phase-synchronized with a reference clock output from an image pickup device incorporated in a detachably connected endoscope, by using a phase-locked loop circuit in which a phase comparator compares a phase of a variable clock generated in a voltage controlled oscillation circuit with a phase of the reference clock, comprising:

a gate opening/closing control step of changing a gate at least from a closed state to an open state for input of the reference clock to the phase comparator;

an operation control signal step of generating an operation control signal for setting the phase-locked loop circuit in a closed loop operable state during intermittent periods;

a sync timing setting step of synchronizing a timing of starting the generation of the operation control signal with a timing of input of the variable clock to the phase comparator at least within a predetermined time period shorter than half of the cycle T of the variable clock; and a sync detection step of performing detection as to whether or not the variable clock is phase-synchronized with the reference clock, wherein, if the cycle of the variable clock is T, the predetermined time period is set in the sync timing setting step so that the timing of starting the generation of the operation control signal is set within a range from T/4 to less than T/2 from the timing of input of the variable clock to the phase comparator so as to operate, when set to an operation state of the closed loop, in a direction to decrease, in terms of frequency, a relative phase difference of the variable clock with respect to the reference clock before the operation state of the closed loop.

17. The endoscope signal processing method according to claim 16, wherein, if the time period during which the variable clock is not phase-synchronized with the reference clock exceeds a predetermined time period as a result of detection in the sync detection step, change from the gate open state to the gate closed state is temporarily made and the gate opening/closing control step is thereafter performed.

* * * * *